US008563752B2

(12) United States Patent
Hanselmann et al.

(10) Patent No.: US 8,563,752 B2
(45) Date of Patent: *Oct. 22, 2013

(54) PROCESS FOR THE PRODUCTION OF CARNITINE BY CYCLOADDITION

(75) Inventors: Paul Hanselmann, Brig-Glis (CH); Ellen Klegraf, Brig-Glis (CH); Stephan Elzner, Brig-Glis (CH); Wilhelm Quittmann, Visp (CH); Daniel Friedrich Fischer, Visp (CH)

(73) Assignee: Lonza Ltd., Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/186,570

(22) Filed: Jul. 20, 2011

(65) Prior Publication Data

US 2012/0022275 A1     Jan. 26, 2012

Related U.S. Application Data

(60) Provisional application No. 61/366,382, filed on Jul. 21, 2010.

(30) Foreign Application Priority Data

Jul. 21, 2010 (EP) ..................... 10007567

(51) Int. Cl.
  *C07D 305/12* (2006.01)
(52) U.S. Cl.
  USPC .......................................... 549/329
(58) Field of Classification Search
  USPC .......................................... 549/329
  See application file for complete search history.

(56) References Cited

U.S. PATENT DOCUMENTS 6,040,465 A    3/2000  Miyano et al.

FOREIGN PATENT DOCUMENTS

| CH | 680588 A5 | 9/1992 |
| JP | 11255759 | 9/1999 |

OTHER PUBLICATIONS

Carter et al. J. Org. Chem. 1996, 61, 8006-8007 Carter et al. J. Org. Chem. 1996, 61, 8006-8007.*
Nelson et al. J. Am. Chem. Soc. 1999, 121, 9742-9743.*
Lin et al. Organic Letter 2007, 9(4), 567-570.*
Dorwald F. A. Side Reactions in Organic Synthesis, 2005, Wiley: VCH, Weinheim p. IX of Preface p. 1-15.*
Wynberg et al. J. Am. Chem. SOC. 1982, 104, 166-168.*
France et al. Chem. Rev. 2003, 103, 2985-3012.*
Song et al. Tetrahedron Asymmetry. 1995, 6, 1063.*
Nelson, et al., "Catalytic Asymmetric Acyl Halide-Aldehyde Cyclocondensations. A Strategy for Enantioselective Catalyzed Cross Aldol Reaction", J. Am. Chem. Soc., vol. 121, pp. 9742-9743; 1999.
Nelson, et al., "Divergent Reaction Pathways in Amine Additions to β-lactone electrophiles. An Application to β-Peptide Synthesis", Tetrahedron, vol. 58, pp. 7081-7091; 2002.
Shen, et al., "Catalytic Asymmetric Assembly of Stereodefined Propionate Units: An Enantioselective Total Synthesis of (−)-Pironetin", J. Am. Chem. Soc., vol. 128, pp. 7438-7439; 2006.
Nelson, et al., "Enantioselective β-Amino Acid Synthesis Based on Catalyzed Asymmetric Acyl halide-Aldehyde Cyclocondensation Reactions", Angew. Chem. Int. Ed., vol. 39, pp. 1323-1325; 2000.
Santaniello, et al., "Chiral Synthesis of a Component of Amanita Muscaria, (−)-4-Hydroxypyrrolidin-2-one, and Assessment of its Absolute Configuration", J. Chem. Research (S), pp. 132-133; 1984.
Calter., "Catalytic, Asymmetric Dimerization of Methylketene", J. Org. Chem vol. 61, pp. 8006-8007; 1996.
Chidara, et al., "Reaction Rate Acceleration Enabled by Tethered Lewis Acid-Lewis Base Bifunctional Catalysis: A Catalytic, Enantioselective [2+2] Ketene Aldehyde Cycloaddition Reaction", Synlett, vol. 10, pp. 1675-1679; 2009.
Kull, et al., "Practical Enantioselective Synthesis of β-Lactones Catalyzed by Aluminum Bissulfonamide Complexes", Adv. Synth. Catal, vol. 349, pp. 1647-1652; 2007.
Lin, et al., "A Lewis-Acid-Lewis Base Bifunctional Catalyst from a New Mixed Ligand", Organic Letters, vol. 9, No. 4, pp. 567-570; 2007.
Lin, et al., "Predicting the RIS absolute configuration in asymmetric bifunctional catalysis (ABC)", Tetrahedron Letters, 48; pp. 5275-5278; 2007.
Mondal, et al., "Phosphine-Catalyzed Asymmetric Synthesis of β-Lactones from Arylketoketenes and Aromatic Aldehydes", Organic Letters, vol. 12, No. 8; pp. 1664-1667; 2010.
Song, et al., "New Method for the Preparation of (R)-Carnitine", Tetrahedron: Asymmetry, vol. 6, No. 5, pp. 1063-1066; 1995.
Wynberg, et al., "Asymmetric Synthesis of (S)- and (R)-Malic Acid from Ketene and Chloral", J. Am. Chem. Soc., vol. 104, pp. 166-168; 1982.
Zhu, et al., "Cinchona Alkaloid-Lewis Acid Catalyst Systems for Enantioselective Ketene-Aldehyde Cycloadditions", J. Am. Chem. Soc., vol. 126, pp. 5352-5353; 2004.

* cited by examiner

*Primary Examiner* — Nizal Chandrakumar
(74) *Attorney, Agent, or Firm* — Hoffmann & Baron, LLP

(57) ABSTRACT

The invention relates to a method for the production of L-carnitine, wherein a chiral β-lactone carnitine precursor is obtained by a [2+2] cycloaddition of ketene with an aldehyde X—CH$_2$—CHO, wherein X is selected from Cl, Br, I and trimethylamine, in the presence of a chiral catalyst.

20 Claims, No Drawings

PROCESS FOR THE PRODUCTION OF CARNITINE BY CYCLOADDITION

CROSS-REFERENCE TO RELATED APPLICATION

This application claims the benefit of priority from European Patent Application No. 10007567.0 filed Jul. 21, 2010 and U.S. Provisional Patent Application No. 61/366,382 filed Jul. 21, 2010, which are incorporated herein by reference.

The invention relates to methods for the production of L-carnitine.

BACKGROUND OF THE INVENTION

Carnitine (vitamin Bt; 3-hydroxy-4-trimethylammoniobutanoate) is a quaternary ammonium compound biosynthesized from the amino acids lysine and methionine. In living cells, it is required for the transport of fatty acids from the cytosol into the mitochondria during the breakdown of lipids for the generation of metabolic energy. It is used as a nutritional supplement. Carnitine exists in two stereoisomers. The biologically active form is L-carnitine, whilst its enantiomer, D-carnitine, is biologically inactive. When producing L-carnitine in an industrial process, it is desirable to produce the biologically active L-form in high purity.

Various methods were described for the industrial production of L-carnitine. Microbiological processes are known, in which L-carnitine is produced directly by bacteria. In other processes, a racemate is produced by organic synthesis and separated subsequently into enantiomers.

Methods have been described for producing L-carnitine by chiral synthesis in the presence of asymmetric catalysts. In this respect, Santaniello et al. (1984) disclose the direct production of chiral L-carnitine from various precursors. In a specific approach, a ketoester corresponding to carnitine is reduced in the presence of an asymmetric catalyst, followed by the reaction of the product with trimethylamine in order to obtain L-carnitine. The authors also suggest producing L-carnitine from a β-lactam cyclic precursor.

Attempts have been made to synthesize. L-carnitine from β-lactone intermediates. In principle, β-lactones are available by [2+2] cycloadditions of ketenes and aldehydes. Chiral catalysts for obtaining chiral β-lactones were originally described by Wynberg et al. (1982). The authors found that a cycloaddition reaction could be carried out in the presence of a chiral quinidine catalyst. However, the availability of β-lactones suitable for carnitine synthesis is severely limited, because the reactions usually require activated ketones or aldehydes.

Based on the findings of Wynberg et al., Song et al. (1995) developed a full synthesis of L-carnitine starting from chloral (trichloroethanal) and ketene. The overall reaction is shown in scheme 1 below.

Scheme 1: Synthesis of L-carnitine according to Song et al., 1995.

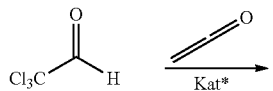

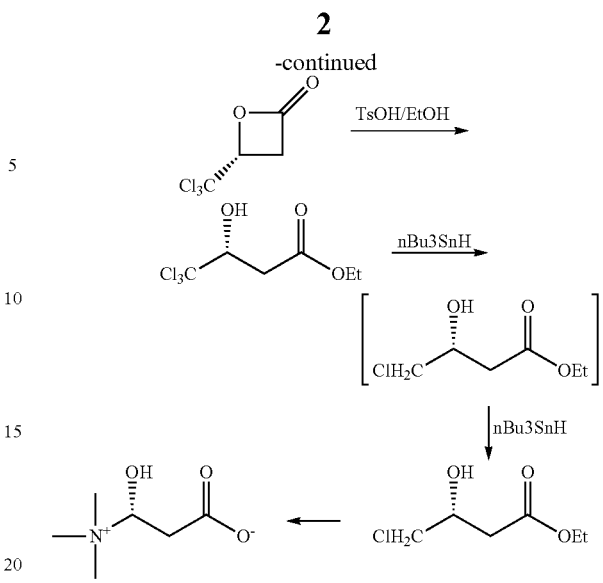

After the ring opening reaction, two chlorine atoms have to be eliminated from the carnitine precursor. Several steps are necessary to convert the trichloral ester into the corresponding monochlorinated equivalent before final conversion into carnitine. This renders the overall process time consuming and complicated. Further, the method requires chloral and tin organic reactants, which are toxic. Since carnitine is usually required for food or feed applications, it is desirable to avoid such toxic substances. Further, n—$Bu_3SnH$ has to be produced in situ, which is relatively complicated. In view of these drawbacks, the industrial applicability of this pathway is severely limited.

Since chiral L-carnitine is an important industrial product, it would be desirable to provide alternative efficient processes for its production. Specifically, it would be desirable to provide processes which allow the production of L-carnitine in a relatively simple manner and at a high yield.

Problem Underlying the Invention

The problem underlying the invention is to provide a method for producing L-carnitine, which overcomes the above-mentioned drawbacks. Specifically, the problem is to provide an efficient and simple process for the production of L-carnitine.

The total yield as well as the chiral yield shall be high. Further, the necessary chemicals shall be readily available and should not be too expensive. Specifically, the use of catalysts comprising precious metals, such as platinum, shall be avoided.

The number of process steps shall be relatively low and the process shall not require complicated apparatuses. Overall, the process shall be cost and labour efficient.

DESCRIPTION OF THE INVENTION

Surprisingly, the problem underlying the invention is solved by the process according to the claims. Further inventive embodiments are disclosed throughout the description.

Subject of the invention is a process for the production of L-carnitine, wherein a chiral β-lactone carnitine precursor is obtained by a [2+2] cycloaddition of ketene with an aldehyde X—$CH_2$—CHO, wherein X is selected from Cl, Br, I and trimethylammonium, in the presence of a chiral catalyst.

Ketene (ethenone, formula $C_2H_2O$) is a colorless gas, which is highly reactive due to two adjacent double bonds in the molecule.

According to the invention, a direct and simple synthesis of carnitine is carried out starting from monohalogenated acetaldehyde or from trimethylammonium acetaldehyde in a [2+2] cycloaddition. The chiral β-lactone obtained thereby can be converted directly into L-carnitine.

Surprisingly it was found that chiral P-lactones, which can be simply converted into L-carnitine, can be obtained in the presence of chiral catalysts. Chiral catalysts usually comprise at least one asymmetric atom. However, other chiral catalysts are known, which are chiral although not comprising a chiral C-atom, for example BINAP. They interact with the reactants in a manner such that chiral products are obtained instead of a racemate. When the ketene reacts with the aldehyde in a [2+2] cycloaddition in the presence of a chiral catalyst, a chiral β-lactone is obtained. The chiral β-lactone is a substituted 4-methyloxetane-2-one, which has the residue R attached to the methyl group. Thus, the reaction product, depending on residue R, is 4-(chloromethyl)oxetane-2-one, 4-(bromomethyl)oxetane-2-one, 4-(iodomethyl)oxetane-2-one or 4-[(trimethylammonium)methyl]oxetane-2-one.

In a preferred embodiment of the invention, the chiral catalyst is selected from Lewis acid-Lewis base bifunctional metal catalysts and phosphine catalysts.

Preferably, the chiral catalyst is a Lewis acid-Lewis base bifunctional metal catalyst. The Lewis acid and Lewis base can either be separate compounds or can be associated with each other by ionic, covalent or other interactions, for example in a metal complex. When being separate components, the Lewis acid and Lewis base are associated with each other at least in the catalytic state in order to catalyze the enantioselective reaction. The Lewis acids are preferably metal atoms, metal ions or metal salts and the Lewis bases are chiral organic ligands, usually comprising amine, phosphine, alcohol and/or amide groups. The catalysts are bifunctional, because the chirality is a property of the ligands and thus independent from the Lewis base. Therefore, the bifunctional catalysts are distinct from chiral metal complex catalysts such as Wilkinson catalyst, in which only the overall complex, but not the ligands themselves, are chiral.

In a preferred embodiment of the invention, the Lewis acid/Lewis base bifunctional catalyst comprises a metal atom as the Lewis acid. The Lewis acid may be provided in the form of an ion, a salt or a metal complex. One, two or more ligands may be attached to the metal to form a metal complex. In a preferred embodiment of the invention, the metal is selected from those of groups (I) and (II) of the periodic table, preferably lithium, sodium, potassium, magnesium and calcium. Further preferred are silver, gold, cobalt, aluminum, copper, nickel, chromium, iron, tin, zinc, manganese, scandium, titanium and boron. In a more preferred embodiment, the metal is lithium, aluminum or cobalt, especially cobalt (II) or (III).

Preferably, the central cobalt ion has two ligands attached thereto, which may be covalently linked to each other.

The Lewis acid-Lewis base bifunctional metal catalyst may be a metal chelate complex, in which the metal is bound in a fixed position. Alternatively, the Lewis acid and the Lewis base may be separate entities, which can be added separately to the reactants. In this embodiment, a metal complex is formed in situ at least transiently.

When the Lewis acid is an ion or salt of silver or metals of groups (I) or (II) of the periodic table, preferably lithium, it is preferably provided in the form of a salt, especially lithium perchlorate, to the reaction mixture. Preferably, the anion of the salt is chosen such that it does not interfere with the reaction. It should not become a coordinating entity in the Lewis acid/Lewis base complex. This means, that it is not become part of or bind to the catalytic complex and should not contribute to or inhibit the catalytic reaction. Preferred such anions are perchlorate, mesylate, $PF_6^-$ or $BF_4^-$. Suitable anions are also those used in ionic liquids. Preferably, the chiral catalyst comprises a Lewis base selected from chiral amines, chiral phosphines, chiral alcohols and chiral amides.

The chiral amine is preferably an alkaloid, preferably quinine or quinidine, a di-triamine or salen. The chiral phosphine is preferably SEGPHOS or TUNEPHOS.

The chiral phosphine is preferably BINAP. The chiral amide is preferably a bissulfonamide. The chiral catalyst may also be a derivative of any of the above.

Quinine (CAS 130-95-0) and its stereoisomer quinidine (CAS 56-54-2) are heterocyclic aromatic compounds of the formula $C_{20}H_{24}N_2O_2$. Quinine is a natural alkaloid having pharmaceutical properties.

Salen (CAS 94-93-9) is a chelating ligand used in coordination chemistry and homogeneous catalysis. The name salen is a contraction for salicylic aldehyde and ethylenediamine.

The Lewis base may be a derivative of the above mentioned ligands. The term "derivative" relates to ligands, which are chemically altered, but still function as ligands in the complex and provide catalytic activity. For example, derivatives may be those in which have additional residues, such as alkyl, halogen or arylic groups, attached to the basic molecular structure. Further, portions of the molecules may be replaced by other groups. For example, arylic rings may be replaced by heteroarylic rings. However, the derivatives or catalysts comprising the derivatives should have the same or essentially the same catalytic activity as the above mentioned compounds. Preferably, the catalytic activity of the derivative should be at least 50% or at least 100% of the original compound. Derivatives may be designed to improve the stability or the catalytic activity of the chiral catalyst.

In a specific embodiment of the invention, a Lewis acid-Lewis base bifunctional metal catalyst is used having two ligands, which are covalently linked to each other. For example, a salen molecule is covalently linked to a quinine or quinidine molecule, specifically by an ester bond.

In a highly preferred embodiment of the invention, the Lewis acid/Lewis base bifunctional catalyst is a chiral alkaloid in combination with a lithium salt. Preferred respective Lewis acid/Lewis base catalyst systems are disclosed by Calter (1996), Zhu et al. (2004), and Shen et al. (2006). The catalysts comprise cinchona alkaloid Lewis bases and derivatives thereof in combination with lithium perchlorate as a Lewis acid. Usually, the Lewis base and the salt are added separately into the reaction mixture. Thus the catalyst is formed in situ. According to the invention, the alkaloid is preferably a derivative of quinine or quinidine, which is substituted at the chiral 9-position with a bulky substituents. Preferably, the bulky substituents comprises between 3 and 15, more preferably between 4 and 8 carbon and/or silicium atoms. In preferred embodiments, it is selected from branched alkyl groups, such as iso-butyl and tert-butyl, and branched silyl group with alkyl and/or aryl substituents, preferably triarylsilyl groups and trialkylsilyl groups. Especially preferred is (trimethylsilyl)quinine in combination with lithium perchlorate.

The alkaloids are preferably quinine, quinidine or derivatives thereof. Preferred derivatives are propionylquinidine and propionylquinine, and especially preferred are (trimethylsilyl)quinine (TMSQ, shown in scheme 2a) below) and (trimethylsilyl)quinidine (TMSq). The catalysts disclosed in these documents are incorporated herein by reference. Specifically, the catalysts of Calter (1996) in table 1, of Zhu et al. (2004) in FIG. 1 and of Shen et al. (2006) in FIG. 1 are incorporated by reference. Further, the methods and conditions of their use are preferably applied according to the invention.

A preferred group of catalysts comprises a central Al(III) atom, to which two sulfonamide groups and one additional residue are attached. The additional residue is preferably an organic residue, preferably methyl, ethyl or phenyl, or inorganic, such as halide, especially Cl, or CN. Thereby, the Al(III) is coordinated by the respective N-atoms of the sulfonamide groups. The sulfonamide groups may be substituted, preferably with aryl or alkyl groups. Preferably, they are linked to each other through a bridging group. Chirality is conferred to the catalyst either by one or more stereocenters adjacent to nitrogen atom(s) of the sulfonamide groups or by the bridging group. Preferably, such catalysts have the following formula:

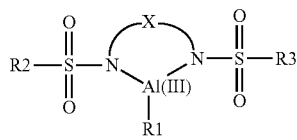

wherein
R1 is alkyl having 1 to 10 carbon atoms, preferably methyl, ethyl, propyl or butyl; or aryl, preferably phenyl; or a halide, such as Cl, or CN
R2 and R3 are independently from each other defined as R1 above, or halogenated alkyl, such as —CF$_3$,
X is an organic bridging group comprising 1 to 20, preferably 1 to 6 atoms, which can be substituted, preferably by aryl, especially phenyl, or alkyl;
  and/or wherein X optionally comprises at least one heteroatom, such as N, O or S;
  and/or wherein X optionally is a cyclic group, such as a cycyoalkyl, preferably cyclohexyl.

In another embodiment of the invention, the bifunctional catalyst comprises a Lewis acid, which is a central aluminum (III), which is attached to Lewis base. In a preferred embodiment, the Lewis base is a chiral triamine compound, optionally in combination with an additional non-chiral ligand. Such catalysts are disclosed by Nelson et al. (1999), Nelson and Spencer (2000) and Nelson et al. (2002). Specifically, aluminum (III) catalysts useful according to the invention are disclosed in Nelson et al., 1999, Fig. (III) on page 9742, and incorporated herein by reference. A catalyst of Nelson et al., 1999, is shown in scheme 2c) below. Further, the specific catalyst disclosed in Nelson and Spencer (2000) in scheme 2 is applicable according to the invention and incorporated by reference. Catalysts from the same class are disclosed in Nelson et al., 2002, FIG. 2, and also incorporated by reference. Further, the methods and conditions of the use of the catalysts according to Nelson and co-workers are preferably applied according to the invention.

In another preferred embodiment, the central aluminum (III) is coordinated with a chiral alcohol, or with chiral phosphines, such as BINAP, SEGPHOS (5,5'-Bis(diphenylphosphino)-4,4'-bi-1,3-benzodioxole) or TUNEPHOS ((R)-1,13-Bis(diphenylphosphino)-7,8-dihydro-6H-dibenzo[fh][1,5] dioxonin; CAS 301847-89-2) or derivatives thereof.

In another preferred embodiment, a central aluminum (III) is coordinated with a chiral amide, preferably an amide comprising two amide groups in a chelate complex. Preferably, the ligand is a bissulfonamide and the catalyst is a bissulfonamide aluminum complex. Such complexes and their use for [2+2] cycloadditions are disclosed in Kull and Peters, 2007. The chiral catalysts disclosed therein, especially in scheme 1 and scheme 3, are incorporated herein by reference. The Lewis acid may be derived from an organoaluminum compound, specifically an alkylaluminum compound, such as DIBAL (diisobutylaluminumhydride) or triethylaluminum. Preferred amide catalysts are shown in scheme 2 e). Other useful amide catalysts, such as the aluminium complex of (1R, 2R)-1,2-N,N-bis(2,4,6-triisopropylbenzenesulfonylamino)-1,2-diphenylethane, are disclosed by U.S. Pat. No. 6,040,465 and JP11255759 and also incorporated herein by reference.

BINAP is an abbreviation for the organophosphorus compound 2,2'-bis(diphenylphosphino)-1,1'-binaphthyl (CAS number of (S)-form: 76189-56-5). BINAP is a chiral ligand, which is used in asymmetric synthesis. It consists of a pair of 2-diphenylphosphinonaphthyl groups linked at the 1 and 1' positions. In formula (I) below, BINAP is the compound in which all R are H.

In another embodiment of the invention, the Lewis acid/Lewis base bifunctional catalyst has the formula

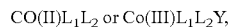

wherein
  L$_1$ is salen or a derivative thereof,
  L$_2$ is quinine or quinidine or a derivative thereof and
  Y is a monovalent anion,
  wherein L$_1$ and L$_2$ are covalently linked, preferably via an ester bond.

In a preferred embodiment, the monovalent anion Y comprises antimony and is more preferably [SbF$_6$]$^-$. Such Lewis acid/Lewis base bifunctional catalysts comprising central cobalt atoms are disclosed by Lin et al. (2007a, 2007b) and Chidara and Lin (2009, see scheme 2b) below). Specifically, herein incorporated by reference is the Lewis acid/Lewis base bifunctional catalyst disclosed by Lin et al (2007a), FIG. 1 (page 568). Further incorporated by reference is the specific asymmetric bifunctional catalyst disclosed in scheme 2 of Lin et al. (2007a) on page 569, which carries a central cobalt atom. These catalysts are also studied in Lin et al (2007b). In these catalysts, a central cobalt atom, preferably cobalt (II) or (III), is bound to a salen and quinidine ligand, both of which are covalently linked to each other via an ester bond. The catalyst thus comprises a central metal atom as a Lewis acid, which provides electrophilic activation of the aldehyde. The chiral Lewis base, which is quinidine, provides asymmetric induction in the reaction. The salen moiety binds the cobalt atom as a planar chelating agent. Further incorporated by reference is the specific catalyst disclosed by Chidara and Lin (2009). As shown in scheme 3 of this publication, the catalyst comprises a central cobalt (III) ion, which is bound to a salen ligand which is covalently attached to quinine or quinidine by an ester bond. Since the cobalt is in oxidative state (III), it carries a positive charge, and thus an anion is comprised, which is [SbF$_6$]$^-$. The general methods and conditions of the use of the catalysts according to Lin and co-workers are preferably applied according to the invention.

In another highly preferred embodiment of the invention, the catalyst is a chiral organic phosphine. Usually, such catalysts comprise in one molecule one, two or more phosphor atoms and one or more aromatic ring systems. Amongst such phosphines, BINAPHANE ((R,R)-1,2-Bis[(R)-4,5-dihydro-3H-binaphtho(1,2-c:2',1'-e)phosphepino]benzene; CAS 253311-88-5; see scheme 2d)) is preferred, either in the R- or S-form. The development and use of BINAPHANE is disclosed by Mondal et al., 2010. Preferably, the general catalytic process conditions disclosed therein are used according to the invention and incorporated herein by reference.

When using a chiral phosphines catalyst, the addition of a Lewis acid is in principle possible, but not necessary.

Scheme 2:

a)

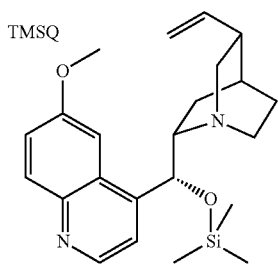

b)

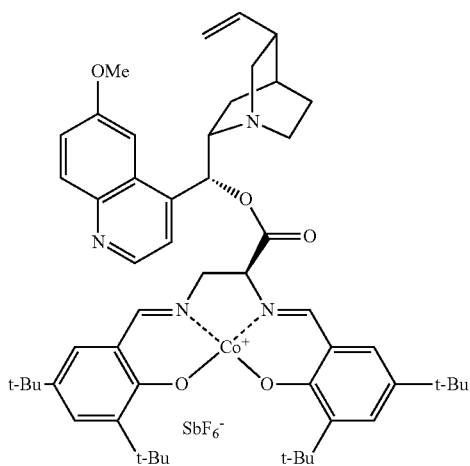

c)

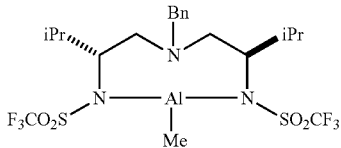

d)

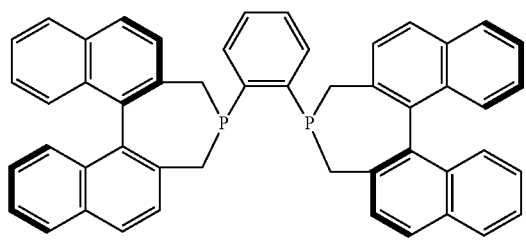

e)

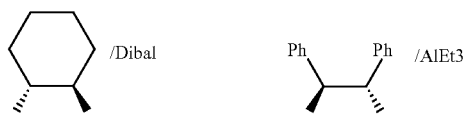

preferred catalysts: a) (trimethylsilyl)quinidine (TMSQ, Calter et al., 1996),
b) Lewis acid/Lewis base bifunctional catalysts with central cobalt atom (Chidara and Lin, 2009),
c) catalyst with central aluminum (III) attached to triamine compound and additional ligand according to Nelson et al., 1999,
d) (R)-BINAPHANE (Mondal et al., 2010),
e) Al-bissulfonamide catalysts according to Kull and Peters, 2007.

From the catalysts mentioned above, the catalysts based on chiral alkaloids in combination with a lithium salt and the chiral phosphine catalyst are especially preferred, because they are relatively easily available and thus eligible for synthesis in an industrial scale.

In preferred embodiment, the catalyst is recycled. The catalyst can then be reused in multiple reactions. The reaction mixture or the solvent can be separated from the catalyst by known methods, such as pervaporation, nanofiltration, membrane separation, membrane filtration, electrodialysis, diafiltration, reverse osmosis, liquid chromatography (LC), HPLC, extraction, crystallization and the like. It is also preferred to immobilize the catalyst on a solid phase, such as a silica support. For example, a catalyst having a free vinyl group, such as a quinine or quinidine vinyl group, could be attached to a silica support by hydrosilylation.

Another subject of the invention is a process for the production of a chiral β-lactone, wherein the chiral β-lactone is obtained by a [2+2] cycloaddition of ketene with an aldehyde X—CH$_2$—CHO, wherein X is selected from Cl, Br, I and trimethylamine, in the presence of a chiral catalyst. The β-lactone is an L-carnitine precursor and thus a valuable intermediate in the synthesis of L-carnitine. The reactants, catalysts, conditions etc. regarding this embodiment are selected as outlined above for the synthesis of L-carnitine.

In a preferred embodiment of the invention, the aldehyde X—CH$_2$—CHO is obtained in a preceding step from 2,4,6-(X—CH$_2$)$_3$-1,3,5-trioxane, wherein X is selected from Cl, Br, I and trimethylammonium. It was found that halogenated ethanal can be obtained from the corresponding halogenated 1,3,5-trioxane. In a preferred embodiment, the halogenated trioxane, which carries one halogen atom at each methyl group, is obtained in a preceding step from 2,4,6-methyl-1,3,5-trioxane. Preferably, this reaction is carried out with molecular chlorine. A preferred reaction pathway is shown in the left side of scheme 3 below.

In specific embodiments of the invention, the β-lactone is 4-(chloromethyl)oxetane-2-one, 4-(bromomethyl)oxetane-2-one or 4-(iodomethyl)oxetane-2-one, and the β-lactone is converted to 4-[(trimethylammonium)methyl]oxetanone-2-one. Preferably, the reaction is carried out with trimethylamine (TMA).

The β-lactones obtained according to the inventive process are converted into L-carnitine. The reaction requires opening of the β-lactone ring.

In a specific embodiment of the invention, the β-lactone is 4-[(trimethylammonium)methyl]oxetanone-2-one, and is hydrolyzed in a ring opening reaction in order to obtain L-carnitine directly. The ring opening reaction can be carried out according to known methods, for example in the presence of a base, preferably in sodium hydroxide solution.

In preferred embodiments of the invention, the β-lactone is 4-(chloromethyl)oxetane-2-one, 4-(bromomethyl)oxetane-2-one or 4-(iodomethyl)oxetane-2-one. The use of 4-(chloromethyl)oxetane-2-one is preferred. The β-lactone is a chiral β-lactone. L-carnitine is available when the (R)-β-lactone is used. The lactone ring is opened by hydrolysis and the halogen atom is substituted by a trimethylammonium group in the presence of trimethylamine (TMA).

The β-lactone obtained according to the inventive reaction may be isolated or purified before the ring opening reaction. Alternatively, the reaction product of the cycloaddition may be subjected to the ring opening reaction without purification of the β-lactone, if required after a pre-treatment, such as a quenching or neutralization step. In this embodiment, it is preferred to add the reaction product comprising the β-lactone to an aqueous mixture comprising a metal hydroxide and TMA. Preferably, this reaction is carried out in a two-step pathway according to the state of the art or in a novel one step pathway.

In the two step pathway, which is disclosed in CH 680 588 A5, the halogenated β-lactone is hydrolysed, usually under basic conditions, in a first step to obtain 4-halo-3-hydroxybutyric acid. In a second step, the acid is converted into L-carnitine with TMA.

Surprisingly, it was found according to the invention that the hydrolysis of the β-lactone and reaction with TMA can be carried out in one step. Preferably, the β-lactone is not subjected to a basic hydrolysis step before being contacted with the trimethylamine. In the reaction, the β-lactone ring is opened and the halogen atom is substituted with a trimethylamine group in a nucleophilic substitution reaction. The halogenated β-lactone can be converted into L-carnitine without a basic hydrolysis before the TMA addition. The TMA can be brought into contact with the β-lactone together with an additional base for basic hydrolysis, or the reaction can be carried out without an addition of an additional base at all, or an additional base for basic hydrolysis might be added after bringing the β-lactone in contact with the TMA. Scheme 1 below shows an exemplified inventive reaction for the production of carnitine, in which a chlorinated β-lactone is brought into contact with a combination of TMA and aqueous NaOH as a hydrolytic base.

Scheme 1: Synthesis of L-carnitine by cleavage of a cyclic β-lactone.

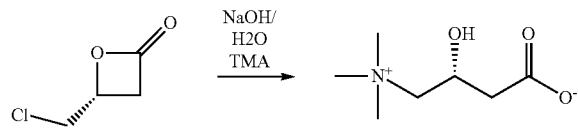

The prior art requires a two step pathway for ring opening of β-lactones, which is disclosed in CH 680 588 A5. In a first step, the halogenated β-lactone is hydrolysed under basic conditions to obtain 4-halo-3-hydroxybutyric acid. In a second step, the acid is converted into L-carnitine with TMA. This two-step approach was used, because in a one-step reaction numerous side reactions were observed or expected, which concur with the desired reaction and inhibit carnitine formation or at least strongly reduce the yield. The side reaction and side products, which are observed and would be expected when carrying out the basic hydrolysis and the halogen substitution with TMA in one single step, are summarized in scheme 2 below. Scheme 2 illustrates all the side reactions which occur, or could occur in theory, when 4-(chloromethyl)oxetane-2-one is reacted with NaOH and TMA. Scheme 2 thus shows the reaction pathways, which are observed in one single reaction batch. Some of the products, such as the lactone 13, may be transient intermediates. Other compounds, especially hydroxycrotonic acid 8, crotonobetaine 10 and the cyclic lactone 6 and furanone 7 are competitive end products. When analyzing the product mixture of a reaction, it was found that the main impurities within this synthesis are hydroxycrotonic acid 8 and crotonobetaine 10. In principle, the 4-(chloromethyl)oxetane-2-one 4 can enter two reaction pathways in the presence of NaOH and TMA. The first pathway starts with basic hydrolysis of the beta lactone 4 to chlorohydroxybutyric acid 5, which can cyclize giving the hydroxybutyrolactone 6 or after elimination of water forming the furanone 7. Formation of hydroxybutyric acid 8 proceeds via intermediate 9, which results from elimination of water from compound 5. Additionally, furanone 7 can also be formed by cyclization reaction of intermediate 9. Crotonobetaine 10 can be obtained by either L-carnitine 1 eliminating water or by compound 9 reacting undergoing nucleophilic substitution of the chloride by trimethylamine. Also epoxy acid 11 can be formed from L-carnitine 1 or 5 by intramolecular nucleophilic substitution of chloride or ammonium by the alcohol group. As both the primary alkylhalogenide in 5 and the ammonium group in L-carnitine 1 represent good leaving groups, a side reaction is their nucleophilic substitution by hydroxide giving the diol 12. The second pathway starts with the amination of the chloro-β-lactone 4 to intermediate 13, which is hydrolyzed with sodium hydroxide to L-carnitine 1. Especially by having not the right reaction conditions, L-carnitine 1 can also undergo further reactions such as cyclization and elimination giving side products 6 and 7 or the above mentioned elimination yielding compound 10.

Scheme 2: Potential reactions of 4-(chloromethyl)oxetane-2-one upon contact with a combination of NaOH and TMA. According to the invention, side reactions can be suppressed and carnitine 1 is obtained as the main product.

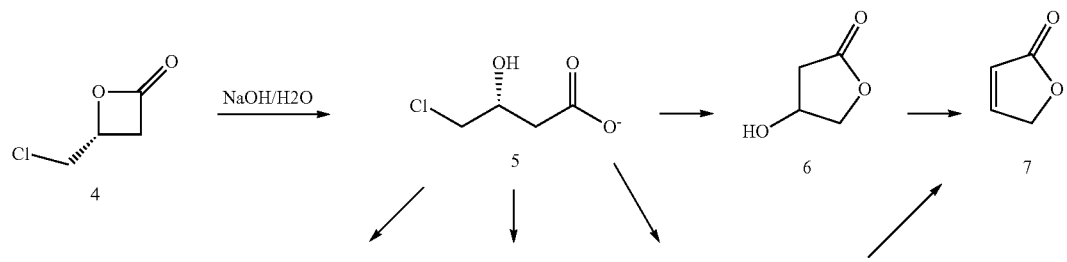

-continued

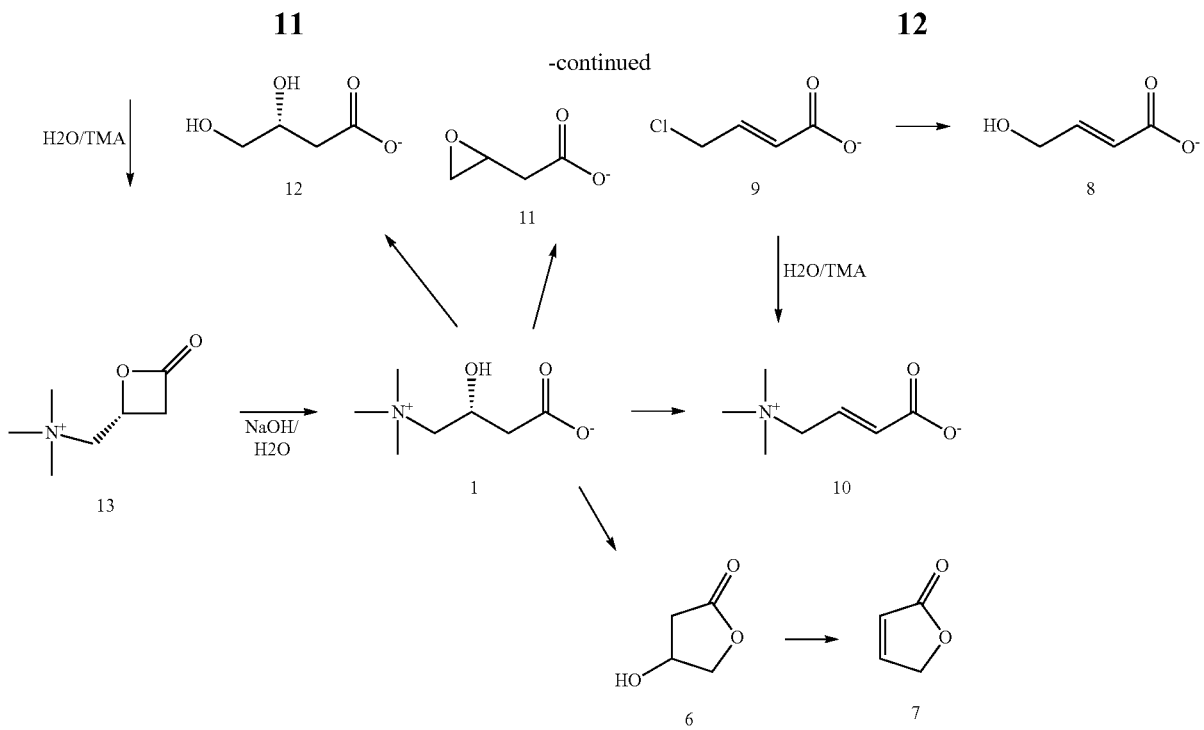

In summary, scheme 2 shows that a multitude of reactions occurs, or would at least be expected, when carrying out a basic hydrolysis of the β-lactone and the nucleophilic substitution reaction with TMA at the same time in one batch. The skilled person would not have expected that both reactions could be carried out efficiently at the same time in the same batch, i. e. that the addition of the TMA and an additional base together would yield carnitine in high amounts. In contrast, he would have expected that especially hydroxycrotonic acid 8 and crotonobetaine 10 and cyclic lactones 6 and 7 would be obtained at significant high yields. Indeed, in initial experiments it was found that the addition of a combination of NaOH with TMA to the β-lactone precursor did not yield L-carnitine in relevant amounts, but various side products as shown in scheme 2 instead. Surprisingly, it was found in further experiments that upon variation of the process conditions (as outlined further below and as shown in the examples), a selective shift of the overall reactions towards L-carnitine production in high amounts occurred. It is unusual that two different process steps can be combined in one single step in a reaction, which is as complicated as outlined above and as illustrated by scheme 2.

According to the invention, the basic hydrolysis (ring opening reaction) and reaction with trimethylamine are preferably carried out in one process step. An additional base different from TMA may be added for the basic hydrolysis. Alternatively, the conditions can be adjusted such that the base TMA itself triggers the basic hydrolysis. In this embodiment, it is not necessary to add an additional base.

In a preferred embodiment, an additional base is added, which is preferably a metal hydroxide. In this embodiment, the β-lactone should be brought into contact with the additional base and with the trimethylamine essentially at the same time. Preferably, the additional base and the trimethylamine are added at the same time, preferably in the form of a mixture, such as a solution or suspension, of metal hydroxide and trimethylamine, or by adding a metal hydroxide solution whilst passing gaseous TMA through the reaction mixture.

When added at the same time, the metal hydroxide triggers the basic hydrolysis and the trimethylamine reacts with the β-lactone by replacing the halogen atom in a nucleophilic substitution. The term "essentially" expresses, that it is not necessary that both components are added precisely at the same time. In principle, both components can be added to the reaction mixture one after the other within a short time span. However, the metal hydroxide should be added before the trimethylamine has considerably reacted in a nucleophilic substitution, or vice versa the trimethylamine should be added before the metal hydroxide has considerably reacted in the ring opening reaction. Thus, both components also can to be added one after the other, as long as it is ensured that both reactions are carried out simultaneously, or at least that 90% or 95% of the reactions are carried out simultaneously. Especially when it is ensured that the reactions do not proceed or proceeds slowly, for example due to a low temperature, it is possible to add one component first and the second component subsequently. When adding the metal hydroxide before the TMA, it should be ensured that no basic hydrolysis occurs before the TMA is added, or that only a neglectable basic hydrolysis occurs, for example of less than 5% of the total β-lactone.

In a preferred embodiment, the basic hydrolysis is carried out by adding a metal hydroxide, preferably sodium hydroxide. In principle, the basic hydrolysis is an ester hydrolysis reaction and reactants know in the art can be used for this step. Thus the basic hydrolysis can also be carried out with other bases, for example potassium hydroxide, lithium hydroxide, calcium hydroxide or magnesium hydroxide.

Preferably, the solvent used according to the invention is water. Alternatively, the reaction can be carried out in a two-phase system comprising water and an organic solvent. In another embodiment, the reaction may be carried out without water in an organic solvent, for example an alcohol, such as ethanol. In this embodiment, a base is added which is free of water or essentially free of water.

In a preferred embodiment, the amount of the additional base, especially the metal hydroxide, is 1.1 to 1.6 equivalents, preferably 1.2 to 1.4 equivalents, based on the initial amount of β-lactone. As outlined above, the basic hydrolysis is an ester hydrolysis reaction, which is in principle well known in the art. However, the basic hydrolysis of an ester according to the state of the art is commonly carried out with a high surplus of a base, for example with a metal hydroxide, such as sodium hydroxide, in a surplus of about 3 to 4 equivalents. Surprisingly, it was found according to the invention that the yield of carnitine is low when such a high stoichiometric excess of a base is added. According to the invention, it was found that a low surplus of a base is advantageous for selectively obtaining carnitine and for suppressing the formation of side products.

Preferably, the reaction is carried out at a temperature between −20° C. and 40° C., preferably between 0° C. and 25° C., preferably at about 0° C. and/or about 25° C. In a preferred embodiment, the temperature is increased during the process, for example from about 0° C. to about 25° C. In a preferred embodiment, the reaction is carried out at normal pressure. Thus, energy can be saved, which is important for industrial scale production.

Preferably, the β-lactone is brought into contact with an aqueous solution comprising a metal hydroxide and TMA. The concentration of the metal hydroxide in the aqueous solution may be between 1 and 20 wt. %, preferably between 2 and 10 wt. %. The concentration of the TMA in the aqueous solution may be between 2 and 15 wt. %, preferably between 3 and 10 wt. %. The δ-lactone may be provided in pure form or in an aqueous solution, for example at a concentration between 1 and 80%, preferably between 5 and 50%. It is preferred that the reaction of the β-lactone with TMA and metal hydroxide in aqueous solution is carried out at room temperature or between 0 and 40° C. The reaction time may be between 20 minutes and 5 hours, preferably between 30 minutes and 3 hours. In this embodiment, enhanced pressure is not necessary. Thus, the reaction can be carried out at low temperatures and without enhanced pressure and is energy-efficient.

Preferably, the β-lactone is added to the aqueous solution comprising TMA and a metal hydroxide. The β-lactone or β-lactone comprising aqueous solution may be added slowly, for example over a time span of 10 minutes to 4 hours, preferably dropwise.

In another preferred embodiment, a solution of the β-lactone in an organic solvent is provided and mixed with an aqueous solution comprising TMA and a metal hydroxide. In this embodiment, the reaction is proceeds in a biphasic system. Preferred organic solvents are tert-butylmethylether (MTBE), dichloromethane (DCM), dichloroethylene (DCE), chloroform, chlorobenzene or toluene. However, other solvents are also appropriate which form a separate organic phase and which do not interfere with the reaction. In theory, chlorinated solvents might react with TMA. Although this was not observed, it would be acceptable, if the production of carnitine is not severely inhibited. The concentration of the β-lactone in the organic solvent may be between 2 and 50 wt. %, preferably between 5 and 20 wt. %. In this embodiment, a surplus of about 1.5 to 4 equivalents, preferably between 2 and 3 equivalents of TMA, may be used. The two-phase reaction can be carried out at low temperatures, for example between −20 and 40° C., or between 0 and 25° C., preferably at 0° C.

Preferably, the TMA is recycled during the process. Since TMA is available in gaseous form, it can be led through the reaction fluid, collected and recycled. In the reaction medium, dissolved TMA can be separated from the mixture after reaction is finished (e. g. by distillation) and reintroduced in the process. Preferably, the TMA is reintroduced into the reaction pathway in a cyclic process. TMA is commercially available in the form of a pure gas (Fluka Chemicals) or in the form of an aqueous solution of 10 to 40 wt. %. The amount of TMA in the reaction mixture may be between 1 and 3 equivalents, preferably between 1 and 2.5 equivalents. However, the amount and excess of TMA is less critical than the amount of metal hydroxide, because it can be recycled during the reaction and reintroduced into the reaction chamber.

In a preferred embodiment, the reaction mixture consists of the β-lactone, water, metal hydroxide and TMA. Additional components may be present at a level below 1% or below 2%. When only using this composition, the reaction mixture is simple and side reactions are minimized.

In a specific embodiment, the basic hydrolysis is mediated by the TMA and no additional base is added for basic hydrolysis. Preferably, this reaction is carried out at enhanced pressure and/or at least in part at enhanced temperature. In a specific embodiment, the solvent is ethanol and the reaction intermediate product is an ethylester of carnitine, which is subsequently hydrolyzed to carnitine. In a specific embodiment of the invention, the solvent is an alcohol and the reaction product is an ester, which is subsequently subjected to a basic hydrolysis.

In this embodiment without an additional base, it is preferred to carry out the reaction at enhanced pressure, preferably in an autoclave. For example, the pressure may be between 2 and 200 bar, especially between 5 and 150 bar or between 10 and 100 bar. The application of enhanced pressure is preferred when the reaction is carried out without an additional base for basic hydrolysis. The hydrolysis reaction with the weak base TMA, which is gaseous, is promoted upon increased pressure.

In this embodiment without an additional base and at enhanced pressure, it is preferred to carry out the reaction at least in part at enhanced temperature, for example between 50° C. and 120° C., more preferably between 80° C. and 100° C. The initial temperature may be below 0° C. and may be raised during the reaction.

In a preferred embodiment of the invention, the yield of L-carnitine is at least 75%, more preferably at least 80%, most preferably at least 85 or at least 90%, based on the total amount of β-lactone. The yield refers to the chiral yield or to the total yield. Preferably, the yield of L-carnitine in the overall reaction starting from the ketene and aldehyde is at least 30%, more preferably at least 40% or 50%, based on the total amount of aldehyde. The yield of L-carnitine based on total carnitine obtained is preferably at least 75%, more preferably at least 85%.

Scheme 3: Exemplified routes for L-carnitine synthesis.

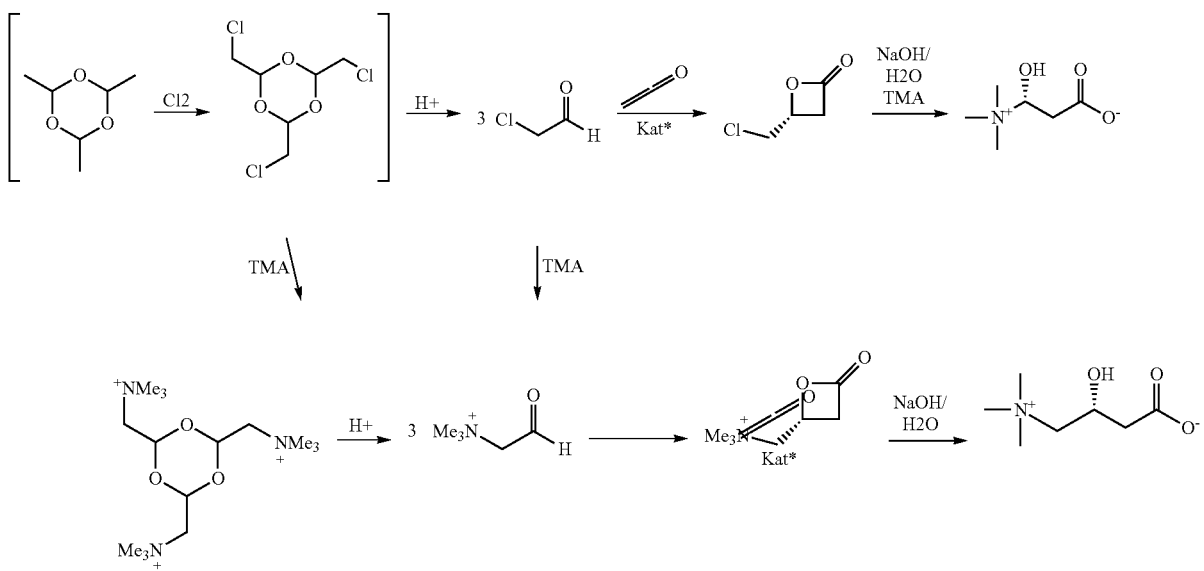

In scheme 3, a preferred reaction route according to the invention is disclosed. Chloroethanal can be obtained in a preceding step from the corresponding trioxane (see upper pathway). The trioxane can be obtained by chlorination of a trimethyltrioxane. The chloroethanal can react with ketene in a [2+2] cycloaddition to obtain the corresponding chiral r3-lactone. L-carnitine is obtained upon basic hydrolysis of the β-lactone in the presence of TMA. Alternatively, the chiral β-lactone can be obtained from a trimethylammonium aldehyde precursor (see bottom pathway). For example, the trichloromethyltrioxane can be converted to the corresponding trimethylammonium trioxane, which subsequently reacts with ketene to the β-lactone. Upon basic hydrolysis and addition of TMA, L-carnitine is obtained.

The inventive process thus solves the problems underlying the invention. The process is relatively simple and economic and requires only a low number of process steps. Thus side reactions are avoided and the total yield and enantiomeric yield are high. The L-carnitine can be obtained without using tin organic compounds or other toxic reactants, which would be problematic in a food or feed product. The use of precious metal catalysts is not necessary. Alternative pathways are available which provide more flexibility for carrying out the process. When comparing the overall reaction to the reaction of Song et al. (scheme 1), it is obvious that the overall process requires less process steps and is more economic. The method of the invention does not require toxic tin organic chemicals, which renders the method more appropriate for producing the food additive carnitine. It is a further advantage of the reaction of the invention that alternative pathways are available, which each yield the desired product. According to the invention, a precursor molecule can either be aminated before or after the cyclization step.

EXAMPLES

L-carnitine was produced from chloroethanal and ketene. The reaction pathway is shown in scheme 4 below.

Scheme 4: Reaction pathway of carnitine synthesis according to examples 1 and 2.

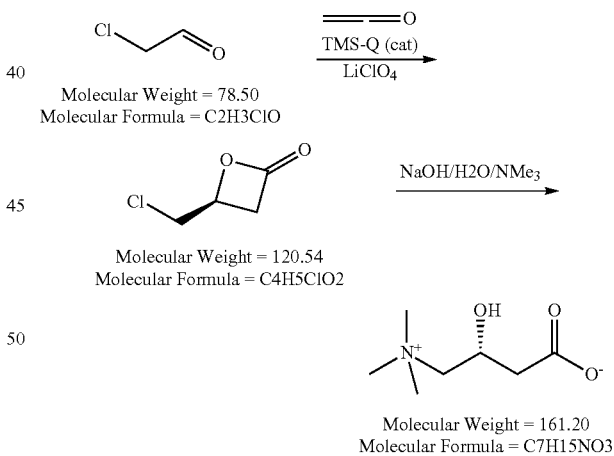

Analytical Methods:

The reaction and the ED are monitored by HPLC on a cation exchange column with UV- and conductometric detection.

Assay carnitine: HPLC, cation exchange column, UV and conductivity detection eluent: acidified water/acetonitrile, using both D- and L-carnitine as a standard. Enantiomeric purity: the product is derivatized using a chiral, fluorescent reagent. The reaction mixture is analyzed by HPLC using an ODS-column and flourimetric detection.

Example 1

Synthesis of β-lactone

A TMSQ catalyst (see scheme 2b) above) was prepared according to the method of Michael A. Calter, J. Org. Chem. 1996, 61, 8006-8007. The catalyst was used in the following [2+2] cycloaddition reaction. In a 500 ml double jacketed reactor (equipped with over head stirrer, cryostate for cooling, nitrogen inlet; ketene dip tube) under nitrogen atmosphere, methylene chloride and a solution of a chloroacetaldehyd in methylene chloride (10.0 g dissolved in 135 g DCM) are charged. The solution is cooled to −50° C. followed by addition of 5.16 g (TMS Quinine, dissolved in 55.17 g methylene chloride) and 4.09 g $LiClO_4$ (dissolved in 54.1 g DCM and 18.0 g THF). Ketene is bubbled through the solution (7 g/h) for 2 h. The reaction is followed by online IR (characteristic wave number of product approx 1832). The reaction is quenched with saturated aqueous bicarbonate solution (579.1 g). After separation of layers, the organic layer is dried with MgSO4 and evaporated to dryness in vacuo. The crude β-lactone is used for the next step without further purification.

Example 2

Conversion of Reaction Product to L-carnitine

The crude product is added to an aqueous solution of NaOH and TMA (water 95.0 g, NaOH 7.3 g, TMA 45% in water 20.8g,) at 0° C. The reaction is stirred at that temperature for 1 h and warmed up to room temperature. Stirring is continued for 1 h. HPLC and IC quoted 40% conversion to carnitine (over 2 steps) with an L-carnitine assay of 85.5.

Example 3

Reaction in a Biphasic System 4-(chloromethyl)oxetane-2-one (10 wt% in organic solvent DCM or toluene) is treated with a mixture of 2.5 eq. of TMA (10-40 wt% in H2O) and 1.2-1.4 eq. of NaOH. The two-phase reaction at 0° C. followed by reaction for 1 h at room temperature yields L-carnitine (over 2 steps, dissolved in the aq. phase) in approx. 30% conversion with an L-carnitine assay of 85%. Main side product is hydroxycrotonic acid.

Example 4

Reaction without NaOH

A solution of lactone in water (50 wt %) is treated with 1.2 eq. of TMA at <−10° C. and autoclaved. The reaction mixture is heated to 90° C. HPLC and IC quoted carnitine (over 2 steps) with an L-carnitine assay of 82%. Main side product is hydroxycrotonic acid.

Example 5

Reaction at Low Temperature

An aqueous solution of sodium hydroxide (1.4 eq) and TMA (1.2 eq) is prepared and cooled to 0° C. At that temperature the β-lactone is added within 1 h. The reaction mixture is stirred further for 1 to 2 h, warmed up to room temperature and analyzed. HPLC and IC quoted 23% conversion to carnitine (over 2 steps) with an L-carnitine assay of 84.6%. Main side product is hydroxycrotonic acid.

Example 6

Conversion of Reaction Product to L-carnitine

To the crude product an aqueous solution of NaOH and TMA (water 95.0 g, NaOH 7.3 g, TMA 45% in water 20.8g,) is added at 0° C. The reaction is stirred at that temperature for 1 h and warmed up to room temperature. Stirring is continued for 1 h. HPLC and IC quoted 40% conversion to carnitine (over 2 steps) with an L-carnitine assay of 85.5%.

Example 7

Synthesis of L-carnitine

In a pre-cooled double jacketed 2 L reactor (with overhead stirring, addition funnel, internal temperature control and inline IR, purged with nitrogen) 3.38 g of $LiClO_4$ in 14.5 g THF and 43.4 g methylene chloride were charged followed by the addition of TMSQ in methylene chloride (2 g in 100 ml DCM). When the inner temperature reached −30° C. aldehyde addition was started (Amount: 198 g of 20 wt-% chloroacetaldehyd in DCM, dosage range: 198 g within 40 minutes) followed by ketene gas addition (ketene flow: 32 g/h; time of dosage: 47 min). The reaction is followed by online IR (characteristic wave number of product approx. 1832). The reaction is quenched with aqueous bicarbonate solution (10%, 254 g). After is separation of layers, the organic layer is dried with $MgSO_4$ (NMR sample showed 32% conversion to beta-lactone, cyclohexane was added as internal standard) and evaporated to dryness in vacuo. The crude β-lactone is used for the next step as for example 6 above without further purification. HPLC and IC quoted 22% conversion to carnitine (over 2 steps) with an ee of 62%.

Example 8

Synthesis of L-carnitine

In a pre-cooled double jacketed 2 L reactor (with overhead stirring, addition funnel, internal temperature control and inline IR, purged with nitrogen) 3.38 g of $LiClO_4$ in 50 ml acetonitrile were charged followed by the addition of TMSQ in methylene chloride (2 g in 100 ml DCM) and 3.5 ml of N,N'-diisopropylethylamine. When the inner temperature reached −30° C. aldehyde addition was started (Amount: 198 g of 20 wt-% chloroacetaldehyd in DCM, dosage range: 198 g within 50 minutes) followed by ketene gas addition (ketene flow: approx. 26.5 g/h; time of dosage: approx. 50 min). The reaction is followed by inline IR (characteristic wave number of product approx. 1832). The reaction is quenched with aqueous bicarbonate solution (75 g bicarbonate in 400 ml water). After separation of layers, the organic layer is dried with $MgSO_4$ (NMR sample showed 49% conversion to beta-lactone, cyclohexane was added as internal standard) and evaporated to dryness in vacuo. The crude β-lactone is used for the step next as for example 6 without further purification. HPLC and IC quoted 33% conversion to carnitine (over 2 steps) with an ee of 76%.

Example 9

Synthesis of L-carnitine

In a pre-cooled double jacketed 2 L reactor (with overhead stirring, addition funnel, internal temperature control and inline IR, purged with nitrogen) 3.38 g of LiClO$_4$ in 50 ml acetonitrile were charged followed by the addition of TMSQ in acetonitrile (0.5 g in 100 ml DCM) and 7.0 ml of N,N'-diisopropylethylamine. When the inner temperature reached −30° C. aldehyde addition was started (Amount: 198 g of 20 wt-% chloroacetaldehyd in DCM, dosage range: 198 g within 50 minutes) followed by ketene gas addition (ketene flow: approx. 26 g/h; time of dosage: approx. 60 min). The reaction is followed by inline IR (characteristic wave number of product approx. 1832). The reaction is quenched with aqueous bicarbonate solution (75 g bicarbonate in 300 ml water). After separation of layers, the organic layer is dried with MgSO$_4$ (NMR sample showed 24% conversion to beta-lactone, cyclohexane was added as internal standard) and evaporated to dryness in vacuo. The crude β-lactone is used for the next according to example 6 step without further purification. HPLC and IC quoted 20% conversion to carnitine (over 2 steps) with an ee of 58%.

Example 10

Synthesis of L-carnitine

In a pre-cooled double jacketed 2 L reactor (with overhead stirring, addition funnel, internal temperature control and inline IR, purged with nitrogen) 15 ml of LiBF$_4$-solution (1M in acetonitril) and 41 ml acetonitrile were charged followed by the addition of TMSQ in acetonitrile (2 g in 100 ml DCM). When the inner temperature reached −30° C. aldehyde was added to the solution (39.5 g of 20 wt-% chloroacetaldehyd in DCM). Ketene gas was bubbled through the solution (23.6 g/h) for 30 minutes. The reaction is followed by inline IR (characteristic wave number of product approx. 1832). The reaction is quenched with aqueous bicarbonate solution. After separation of layers, the organic layer is dried with MgSO$_4$ (NMR sample showed 81% conversion to beta-lactone, cyclohexane was added as internal standard) and evaporated to dryness in vacuo. The crude β-lactone is used for the next as for example 6 step without further purification. HPLC and IC quoted 49% conversion to carnitine (over 2 steps) with an ee of 81%.

Examples 11 to 13

Synthesis of L-carnitine

A catalyst was prepared according to Nelson et al., 1999. To a solution of the bis-sulfonamide ligand (3.2 g, 5 mmol, 0.05 equiv.) in dry DCM (42.7 g) in a 3-neck flask under argon at RT, trialkylaluminum solution (7.5 mmol, 0.075 equiv.) was added dropwise (AlEt$_3$: 7.5 mL of a 1 M solution in hexane, AlMe$_3$: 3.7 mL of a 2 M solution in toluene), leading to gas evolution, but no significant heat evolution. The resulting, faintly yellowish solution was stirred at RT for 2 hours and then diluted with DCM (213 g).

A pre-cooled 2 L reactor with cooling mantle, overhead stirring, addition funnel, internal temperature control and inline IR, purged with nitrogen, was cooled to the indicated temperature and then charged with the activated catalyst solution and a solution of chloroacetaldehyde (20% w/w in DCM, 1 equiv). Both solutions were added through teflon tubing, using argon pressure. When the indicated internal temperature was reached, ketene gas was bubbled into the solution through a teflon tube. After the end of the ketene addition, the mixture was stirred for another 1 h at the indicated temperature before being drained from the reactor into a vigorously stirred sat. ammonium chloride solution. This mixture was stirred for 30 min or until gas evolution ceded. The phases were separated and the organic phase was dried over MgSO$_4$ (2 min stirring). The solvents were removed under reduced pressure (bath temperature 45-48° C.) yielding an orange oily or semi-solid residue. To determine the yield, cyclohexane (840 mg, 10 mmol) was added as internal standard for NMR (significant signal: multiplet at 4.75 ppm, CHO). Yields for the lactone were determined by NMR using 10 mmol cyclohexane as an internal standard, yields for carnitine were determined by quantitative HPLC with IC-detector. All reactions were carried out with 5 mol % ligand and 7.5 mol % AlR$_3$. The reaction conditions and results for three different experiments are summarized in table 1 below.

TABLE 1

Summary of conditions and results

| Example | Temperature [° C.] | Al-source | Yield lactone/carnitine [%] | ee [%] |
|---|---|---|---|---|
| 11 | −40 | AlEt$_3$ | 62/58 | 54 |
| 12 | −40 | AlMe$_3$ | 34/29 | 87 |
| 13 | −78 | AlMe$_3$ | 45/37 | 94 |

LITERATURE

Calter, Catalytic, Asymmetric Dimerization of Methylketen, J. Org. Chem. 1996, 61, 8006-8007.

Chidara and Lin, Reaction Rate Acceleration Enabled by Tethered Lewis Acid-Lewis Base Bifunctional Catalysis: A Catalytic, Enantioselective [2+2] Ketene Aldehyde Cycloaddition Reaction, Synlett 2009, 10, 1675.

Kull, Peters, Practical Enantioselective Synthesis of β-Lactones Catalyzed by Aluminum Bissulfonamide Complexes, Adv. Synth. Catal. 2007, 349, 1647-1652.

Lin et al., A Lewis acid-Lewis Base Bifunctional Catalyst from a New Mixed Ligand, Org. Lett. 2007, 9, 4, 567.

Lin et al., Predicting the R/S Absolute Configuration in Asymmetric Bifunctional Catalysis (ABC), Tetrahedron Letters 2007, 48, 5275.

Mondal et al., Phosphine-Catalyzed Asymmetric Synthesis of β-Lactones from Arylketones and Aromatic Aldehydes, 2010, Org. Lett., Received Jan. 12, 2010.

Nelson et al., Catalytic Asymmetric Acyl Halide-Aldehyde Cyclocondensations. A Strategy for Enantioselective Catalyst Cross Aldol Reactions, J. Am. Chem. Soc. 1999, 121, 9742.

Nelson and Spencer, Enantioselective β-Amino Acid Synthesis Based on Catalyst Asymmetric Acyl Halide-Aldehyde Cyclocondensation Reactions, 2000, Angew. Chem. Int. At. Ed. 39, 1323-1324.

Nelson et al., 2002, Divergent Reaction Pathways in Amine Additions to β-Lactone Electrophoresis. An Application to β-Peptide Synthesis. Tetrahedron 2002, 58, 7081-7091.

Santaniello et al., Chiral Synthesis of a Component of Amanita muscaria, (−)-4-Hydroxypyrrolidin-2-one, and Assessment of its Absolute Configuration, J. Chem. Res. (S) 1984, 132-133.

Shen et al., Catalytic Asymmetric Assembly of Stereo-Defined Propionate Units: An Enantioselective Synthesis of (−)-Pironetin, J. Am. Chem. Soc. 2006, 128, 7436-7439.

Song et al., Mew Method for the Preparation of R-Carnitine, Tetrahedron Asym. 1995, 6, 1063.

Wynberg and Staring, Asymmetric Synthesis of S- and R-Malic Acid from Ketene and Chloral, J. Am. Chem. Soc. 1982, 104, 166.

Zhu et al, Cinchona Alkaloid-Lewis Acid Catalyst Systems for Enantioselective Ketene-Aldehyde Cycloadditions, J. Am. Chem. Soc. 2004, 126, 5352-5353.

The invention claimed is:

1. A process for the production of L-carnitine, wherein a chiral β-lactone carnitine precursor is obtained by a [2+2] cycloaddition of ketene with an aldehyde X—CH$_2$—CHO, wherein X is selected from Cl and Br in the presence of a chiral catalyst, wherein the chiral catalyst is a Lewis acid-Lewis base bifunctional metal catalyst, wherein the Lewis acid is selected from metal atoms, metal ions and metal salts, wherein the metal is selected from lithium, cobalt and aluminum, wherein the Lewis base is a chiral organic ligand comprising chiral amines, chiral phosphines and/or chiral amides, wherein the chiral amine is an alkaloid, a triainine or salen, wherein the chiral phosphine is SEGPHOS (5,5'-Bis(diphnhylphosphino)-4,4'-bi-1,3-benzodioxole), BINAP (2,2'-bis(diphenylphosphino)-1,1'-binaphthyl) or TUNEPHOS ((R)-1,13-Bis(diphenylphosphino)-7,8-dihydro-6H-dibenzo[f,h][1,5]dioxonin), and wherein the chiral amide is a bissulfonamide.

2. A process for the production of L-carnitine, wherein a chiral β-lactone carnitine precursor is obtained by a [2+2] cycloaddition of ketene with an aldehyde X—CH$_2$—CHO, wherein X is selected from Cl and Br in the presence of a Lewis acid-Lewis base bifunctional metal catalyst, and wherein the Lewis acid/Lewis base bifunctional metal catalyst is a chiral alkaoid in combination with a lithium salt.

3. The process of claim 2, wherein the chiral alkaloid is (trimethylsilyl)quinine and the lithium salt is lithium perchlorate.

4. A process for the production L-carnitine, wherein a chiral β-lactone carnitine precursor is obtained by a [2+2] cycloaddition of ketene with an aldehyde X—CH$_2$—CHO, wherein X is selected from Cl and Br in the presence of a chiral catalyst, wherein the chiral catalyst is is Lewis acid-Lewis base bifunctional metal catalyst, wherein the Lewis acid is selected from metal atoms, metal ions and metal salts, and wherein the Lewis base is a chiral organic ligand, and wherein the chiral Lewis acid/Lewis base bifunctional metal catalyst has the formula

Co(II)L$_1$L$_2$ or Co(III)L$_1$L$_2$Y, wherein

L$_1$ is salen,
L$_2$ is quinine or quinidine and
Y is a monovalent anion,
wherein L$_1$ and L$_2$ are covalently linked, preferably via an ester bond,
or wherein the chiral Lewis acid/Lewis base bifunctional catalyst is an Al(III) complex with at least one chiral triamine ligand.

5. The process of claim 1, wherein the aldehyde X—CH$_2$—CHO is obtained in a preceding step from 2,4,6-(X—CH$_2$)$_3$-1,3,5-trioxane.

6. The process of claim 1, wherein the β-lactone is 4-[(trimethylammonium)methyl]oxetanone-2-one, and wherein the β-lactone is hydrolyzed in a ring opening reaction in order to obtain L-carnitine.

7. The process of claim 1, wherein the β-lactone is a chiral 4-(halomethyl)oxetane-2-one, which is subsequently converted into L-carnitine in a method comprising hydrolysis of the β-lactone and reaction with trimethylamine (TMA).

8. The process of claim 7, wherein the β-lactone is not subjected to a hydrolysis step before being contacted with the trimethylamine.

9. The process of claim 7, wherein a basic hydrolysis and reaction with trimethylamine are carried out in one process step.

10. The process of claim 7, wherein the β-lactone is brought into contact with an aqueous solution comprising a metal hydroxide and trimethylamine, or wherein a solution of the β-lactone in an organic solvent is provided and mixed with an aqueous solution coinprising TMA and a metal hydroxide.

11. The process for the production of a chiral β-lactone, wherein the chiral β-lactone is obtained by a [2+2] cycloaddition ketene with an aldehyde X—CH$_2$—CHO, wherein X is selected from Cl and Br in tho presence of a chiral catalyst, wherein the chiral catalyst is a Lewis acid-Lewis base bifunctional metal catalyst, wherein the Lewis acid is selected from metal atoms, metal ions and metal salts, wherein the metal is selected from lithium, cobalt and aluminum, wherein the Lewis base is a chiral organic ligand comprising chiral amines, chiral phosphines and/or chiral amides, wherein the chiral amine is an alkaloid, a triamine or salen, wherein the chiral phosphine is SEGPHOS (5,5'-Bis(diphenylphosphino)-4,4'-bi-1,3-benzodioxole), BINAP (2,2'-bis(diphenylphosphino)-1,1'-binaphthyl) or TUNEPHOS ((R)-1,13-Bis(diphenylphosphino)-7,8-dihydro-6H-dibenzo[f,h][1,5]dioxonin), and wherein the chiral amide is a bissulfonamide.

12. The process of claim 8, wherein a basic hydrolysis and reaction with trimethylamine are carried out in one process step.

13. The process of claim 8, wherein the β-lactone is brought into contact with an aqueous solution comprising a metal hydroxide and trimethylamine, or wherein a solution of the β-lactone in an organic solvent is provided and mixed with an aqueous solution comprising TMA and a metal hydroxide.

14. The process of claim 9, wherein the β-lactone is brought into contact with an aqueous solution comprising a metal hydroxide and trimethylamine, or wherein a solution of the β-lactone in an organic solvent is provided and mixed with an aqueous solution comprising TMA and a metal hydroxide.

15. The process of claim 1, wherein the yield of L-carnitine, based on the total carnitine obtained, is at least 75%.

16. The process of claim 1, wherein the alkaloid is quinine or quinidine.

17. The process of claim 2, wherein the β-lactone is 4-[(trimethylammonium)methyl]oxetanone-2-one, and wherein the β-lactone is hydrolyzed in a ring opening reaction in order to obtain L-carnitine.

18. The process of claim 2, wherein the β-lactone is a chiral 4-(halomethyl)oxetane-2one, which is subsequently converted into L-carnitine in a method comprising hydrolysis of the β-lactone and reaction with trimethylamine (TMA).

19. The process of claim 4, wherein the β-lactone is 4-[(trimethylammonium)methyl]oxetanone-2-one, and wherein the β-lactone is hydrolyzed in a ring opening reaction in order to obtain L-carnitine.

20. The process of claim 4, wherein the β-lactone is a chiral 4-(halomethyl)oxetane-2one, which is subsequently converted into L-carnitine in a method comprising hydrolysis of the β-lactone and reaction with trimethylamine (TMA).

* * * * *

UNITED STATES PATENT AND TRADEMARK OFFICE
CERTIFICATE OF CORRECTION

PATENT NO. : 8,563,752 B2
APPLICATION NO. : 13/186570
DATED : October 22, 2013
INVENTOR(S) : Hanselmann et al.

It is certified that error appears in the above-identified patent and that said Letters Patent is hereby corrected as shown below:

IN THE SPECIFICATION:

Column 3, line 9:

Now reads: "P-lactones"

Should read: -- β-lactones --

Column 8, line 6:

Now reads: "Et3"

Should read: -- $Et_3$ --

Column 8, line 8:

Now reads: "$SO_2AR$"

Should read: -- $SO_2Ar$ --

Column 13, line 33:

Now reads: "The 8-lactone may"

Should read: -- "The β-lactone may" --

Column 15, line 36:

Now reads: "The r3-lactone."

Should read: -- "The β-lactone." --

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,563,752 B2

IN THE SPECIFICATION:

Column 16, line 20:

Now reads: *(See circled portion.)*

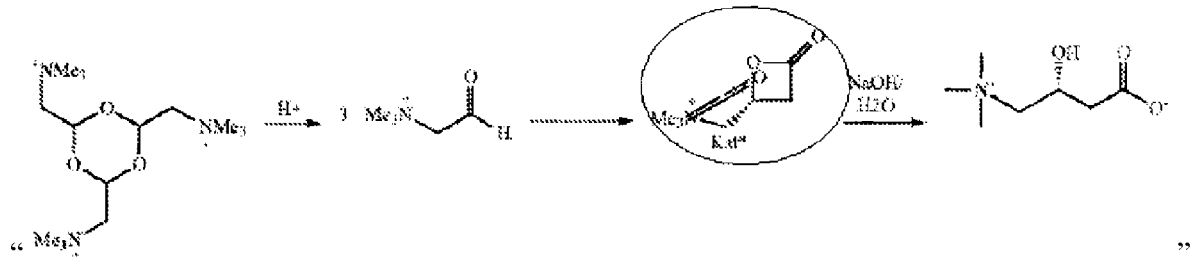

"

Should read:

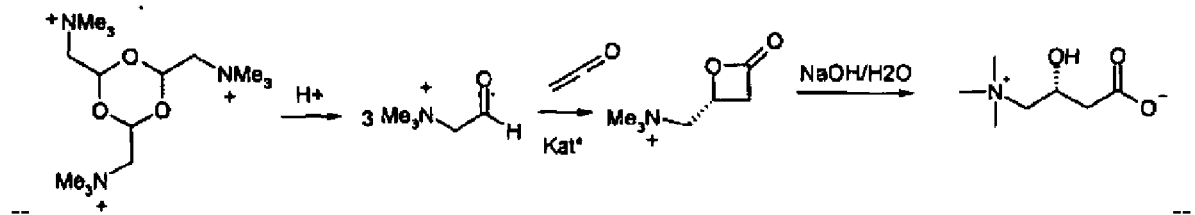

--

Column 21, line 15:

Now reads: "a triainine or salen"

Should read: -- "a triamine or salen" --

Column 22, line 14:

Now reads: "ditionketene with an aldehyde"

Should read: -- "dition of ketene with an aldehyde" --

Column 22, line 16:

Now reads: "in tho presence"

Should read: -- in the presence --